US008545825B2

(12) United States Patent
Moussouni

(10) Patent No.: US 8,545,825 B2
(45) Date of Patent: Oct. 1, 2013

(54) DEPILATORY COMPOSITION IN EMULSION FORM, PROCESS FOR PREPARATION AND USE

(75) Inventor: Farid Moussouni, Hull (GB)

(73) Assignee: Reckitt Benkiser (UK) Limited, Slough, Berkshire (GB)

( * ) Notice: Subject to any disclaimer, the term of this patent is extended or adjusted under 35 U.S.C. 154(b) by 434 days.

(21) Appl. No.: 11/660,817

(22) PCT Filed: Aug. 24, 2005

(86) PCT No.: PCT/GB2005/003294
§ 371 (c)(1),
(2), (4) Date: Feb. 21, 2007

(87) PCT Pub. No.: WO2006/021782
PCT Pub. Date: Mar. 2, 2006

(65) Prior Publication Data
US 2008/0213205 A1    Sep. 4, 2008

(30) Foreign Application Priority Data

Aug. 26, 2004 (GB) .................................. 0419008.8

(51) Int. Cl.
*A61K 8/06* (2006.01)
*A61K 8/81* (2006.01)
*A61Q 9/04* (2006.01)
(52) U.S. Cl.
CPC ............... *A61K 8/8111* (2013.01); *A61Q 9/04* (2013.01)
USPC ...................................................... 424/70.11

(58) Field of Classification Search
None
See application file for complete search history.

(56) References Cited

U.S. PATENT DOCUMENTS

| 5,288,493 | A | | 2/1994 | Martino et al. | |
|---|---|---|---|---|---|
| 5,645,825 | A | * | 7/1997 | Hillebrand et al. | 424/73 |
| 6,203,784 | B1 | * | 3/2001 | Martin et al. | 424/73 |
| 6,468,513 | B1 | * | 10/2002 | Murphy et al. | 424/65 |
| 6,479,043 | B1 | * | 11/2002 | Tietjen et al. | 424/73 |
| 2002/0197292 | A1 | | 12/2002 | Fowler | |
| 2003/0161795 | A1 | * | 8/2003 | Tsuzuki et al. | 424/59 |
| 2003/0206878 | A1 | * | 11/2003 | Gott et al. | 424/63 |

FOREIGN PATENT DOCUMENTS

| WO | WO 95/33439 | 12/1995 |
|---|---|---|
| WO | WO 99/02125 | 1/1999 |
| WO | WO 03/082221 A1 | 10/2003 |

OTHER PUBLICATIONS

PCT International Search Report, PCT/GB2005/003294, dated Nov. 14, 2005.
United Kingdom Combined Search and Examination Report under Sections 17 and 18(3) dated Dec. 9, 2004.
International Preliminary Report on Patentability, PCT/GB2005/003294, dated Feb. 28, 2007.

* cited by examiner

*Primary Examiner* — Brain Gulledge
(74) *Attorney, Agent, or Firm* — Ryan A. Schneider; Troutman Sanders LLP

(57) ABSTRACT

Depilatory compositions comprising a depilatory agent, fatty alcohol and an oil-gelling agent provide improved resistance to rinsing of the compositions from the skin. The compositions provide for a method of depilation in wet conditions using a tool to apply and remove the compositions.

14 Claims, No Drawings

DEPILATORY COMPOSITION IN EMULSION FORM, PROCESS FOR PREPARATION AND USE

CROSS-REFERENCE TO RELATED APPLICATIONS

This is a national phase entry under 35 U.S.C. §371 of International Patent Application PCT/GB2005/003294, filed Aug. 24, 2005, published in English as International Patent Publication WO 2006/021782 A1 on Mar. 2, 2006, which claims the benefit under 35 U.S.C. §119 of Great Britain Patent Application Serial No. 0419008.8 filed Aug. 26, 2004, the entire contents of each of which are hereby incorporated herein by this reference.

TECHNICAL FIELD

The present invention relates to depilatory compositions in the form of an oil-in-water emulsion; their preparation, and methods for their use in removing hair from the skin of humans.

BACKGROUND

Compositions for removing superfluous body hair are known and are of various types. One type of composition requires initial heating before being applied to the skin in a generally molten state. It is then allowed to solidify before being removed from the skin together with unwanted hair. This is known in the art as epilation, as the hairs are uprooted from the skin.

Another type of composition is in the form of a cream, which can be applied to the skin at room temperature. The cream includes a substance that degrades hair keratin. Conventionally, the compositions are applied to the skin where unwanted hair is present, then left in place for a predetermined time to allow the keratin in the hair to become degraded. The composition along with degraded hair is then removed from the skin, usually with a tool such as a sponge or wipe or spatula. Such compositions are known in the art as depilatory compositions.

If the depilatory composition is left in contact with the skin for excessive lengths of time, there is a risk that the composition may cause irritation of the skin in some users. If it is present for too short a time, degradation of keratin may be inadequate, leading to only partial removal of the unwanted hair. In this specification, the period the composition must be left in contact with the hairy skin to achieve adequate hair degradation is referred to as the degradation period. Typical degradation periods are in the range of 3 to 15 minutes.

In the art, the trend has been to make depilatory compositions sufficiently viscous so that they will stay in place on the desired region of skin where superfluous hair removal is desired, without slipping to other regions of skin or falling off during the degradation period. In parallel, there has also been a trend to make the compositions easier to rinse from the skin, so that once the degradation period is over, the composition and degraded hairs can be rinsed easily from the skin. See, for example, EP0855900.

WO 99/02125 discloses depilatory compositions in the form of oil-in-water emulsions. The preferred depilatory compound is cited as potassium thioglycolate. A pH regulator is present, the preferred pH regulator being lime (calcium hydroxide).

A problem with prior art depilatory compositions arises from their ease of rinsing. The user generally applies the compositions in the bathroom by a bathtub, sink or shower, or even in a bath or shower, and must wait for several minutes before removing the composition, but is prevented from simultaneously carrying out any other procedures that could lead to the composition being inadvertently rinsed away or partially rinsed away. This would potentially lead to patches of hair remaining on the skin. So, for instance, with prior art compositions, the user would be inhibited from applying the composition to their legs then washing their upper body, or shampooing their hair, or shaving their armpits during the degradation period. This can lead to a considerable lengthening of the total time required for ablutions when removal of superfluous hair is desired.

It has now been found that these problems can be tackled by providing a depilatory composition that remains in place on the skin for enough time for hair degradation to take place even when rinsed or immersed in water for short periods of time.

DISCLOSURE OF THE INVENTION

In a first aspect, the invention provides a depilatory composition that is an emulsion of hydrophobic particles in a continuous aqueous phase wherein the aqueous phase comprises at least one depilatory agent and the hydrophobic particles comprise a fatty alcohol and an oil-gelling agent.

Surprisingly, the presence of the oil-gelling agent along with the fatty alcohol in the hydrophobic particles of the composition leads to a considerable improvement in the adherence of the composition to the skin, even when subjected to a stream of rinsing water. It is surprising that the oil-gelling agent, which is located in the discrete, hydrophobic particles of the composition, has such an influence on the rinse-ability of the compositions.

In a second aspect, the invention provides a method of hair removal from human skin that includes the steps of: i) applying, preferably with an application tool, a composition according to the first aspect of the invention to the skin where superfluous hair is present, ii) allowing the composition to remain in contact with the skin for a predetermined time, iii) removing the composition and degraded hair, preferably using a removal tool and preferably iv) washing the skin.

Further aspects of the invention are concerned with processes for preparing the depilatory compositions and their use for degrading hair keratin in a wet environment, where there is risk of accidental rinsing away of the composition, such as a bathroom.

The depilatory agent is a substance capable of degrading keratin. The depilatory agent, according to the present invention, may include a mixture of one or more depilatory agents. Preferred depilatory agents are sulfhydryl compounds, meaning a compound having an —S—H group. Suitable sulfhydryl depilatory agents include, but are not limited to, the group consisting of thioglycolic acid, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically and/or pharmaceutically acceptable salts of any of the foregoing compounds.

Preferred sulfhydryl compounds include thioglycolic acid, cysteine, glutathione, N-acetyl-L-cysteine, lipoic acid, thiosalicylic acid, and thiolactic acid and cosmetically and/or pharmaceutically acceptable salts thereof. More preferred sulfhydryl compounds include thioglycolic acid, cysteine, glutathione and N-acetyl-L-cysteine and cosmetically and/or pharmaceutically acceptable salts thereof. The most preferred sulfhydryl compound is thioglycolic acid and cosmetically and/or pharmaceutically acceptable salts thereof. As used herein, "cosmetically and/or pharmaceutically acceptable salts" of the sulfhydryl compounds include, but are not limited to, alkali metal salts, e.g., sodium, lithium, rubidium and potassium salts; alkaline earth metal salts, e.g., magnesium, calcium and strontium salts; non-toxic heavy metal salts, e.g., aluminum salts and zinc salts; boron salts; silicon salts; ammonium salts; trialkylammonium salts, e.g., trimethylammonium and triethylammonium; and tetralkylonium salts.

Preferred cosmetically and/or pharmaceutically acceptable salts of the sulfhydryl compound include sodium, potassium and calcium salts. The most preferred salts of the sulfhydryl compound are potassium and calcium salts.

Suitably, the composition comprises from 1 to 8% by weight, preferably from 2 to 6% by weight, of depilatory agent expressed as the acid form of the depilatory agent. For example, it is preferred that the composition comprises potassium glycolate at pH 12.3, this is not expressed as potassium thioglycolate, but as the equivalent weight of thioglycolic acid.

Optionally, the composition includes an accelerator that will accelerate the keratin degradation reaction. Suitable accelerators include urea, thiourea, dimethyl isosorbide, ethoxydiglycol and methyl propyl diol. Preferably, the accelerator is urea or methyl propyl diol. The composition according to the invention preferably comprises from 5% to 15% by weight, more preferably 7% to 10% by weight of an accelerator.

It is particularly preferred for the composition to comprise a pH regulator to assist in activating the depilatory agent, particularly when the depilatory agent is a sulfhydryl compound. Preferably, the quantity and type of pH regulator is chosen to maintain the pH of the composition at a value greater than 5, preferably greater than 7, more preferably from 8 to 13, most preferably from 10 to 12.9, especially from 12 to 12.7. For example, by ensuring that the pH is about 12.1 to 12.7, depilation can occur within about 5 minutes, as desired by the user, without causing undue irritation. Higher pH levels can lead to irritation problems with some users.

The pH regulator preferably is in the continuous aqueous phase (between the hydrophobic particles) when present. Examples of the pH regulator include arginine (especially L-arginine), silicates (e.g., sodium or potassium silicate), calcium hydroxide and polyethyleneimine. Mixtures of pH regulators may be used. It is particularly preferred for the pH regulator also to include calcium hydroxide in an amount from 2 to 4% by weight of the composition. The pH regulator may be dissolved in the aqueous phase of the composition or may be present as solid particles dispersed throughout the composition.

Compositions according to the invention comprise hydrophobic particles distributed as an emulsion (an oil-in-water emulsion) in an aqueous continuous phase which is a liquid at 25° C. By "aqueous" it is meant that the continuous phase comprises at least 50% by weight of water, preferably 70% by weight or more based on the total weight of the continuous phase. The amount of water in the composition as a whole will typically be from 40% to 95% by weight of the composition.

The hydrophobic particles of the compositions of the invention may comprise non-polar oily or waxy materials that are insoluble in water (by "insoluble" is meant a solubility in water of 0.1% by weight or less at 25° C.) but must comprise a fatty alcohol. Preferably, the alkyl/alkenyl chain of the fatty material is fully saturated. Suitable fatty alcohols comprise from 8 to 22 carbon atoms, more preferably 16 to 22. A mixture of fatty alcohols may also be used. Preferred fatty alcohols include cetyl alcohol, stearyl alcohol and mixtures thereof.

Suitably, the amount of fatty alcohol in compositions of the invention is 3% or more, preferably 5% or more, most preferably 7% or more by weight of the composition. Suitably, compositions of the invention comprise less than 20%, preferably less than 15%, more preferably less than 11% by weight of fatty alcohol.

The hydrophobic particles of the composition further comprise an oil-gelling agent. Suitable oil-gelling agents include waxes having a melting point from 65° C. to 130° C., polymeric-gelling agents and mixtures thereof.

Compositions of the invention suitably comprise from 0.2 to 5%, preferably from 0.5 to 4%, more preferably from 1 to 3% by weight of the oil-gelling agent.

Suitable waxes include beeswax, carnauba, baysberry, candelilla, montan, ozokerite, ceresin, hydrogenated castor oil (castor wax), synthetic waxes such as Fisher-Tropsch waxes, microcrystalline waxes, and mixtures thereof. Waxes such as triglycerides or glycol diesters of $C_{18}$ to $C_{36}$ fatty acids are also suitable as a gelling agent for the oil phase.

Suitable polymeric oil-gelling agents include homopolymers and copolymers of polyethylene, and block copolymers of hydrocarbon-polyether-polyamide or polyether-hydrocarbon types.

A particularly preferred oil-gelling agent is polyethylene in the form of a homopolymer. Preferably, the polyethylene has a molecular weight from 100 to 1000, preferably from 250 to 800, more preferably from 300 to 600 unified mass units. This gives the advantage of ease of incorporation of the polyethylene into the hydrophobic particles of the invention by melting and blending. Polyethylene suitable for use in compositions of the invention is a substantially linear polymer with the structure $CH_3CH_2(CH_2CH_2)_nCH_2CH_3$, where n is a mean number from 2 to 26, preferably from 5 to 15. Preferably, at least 90% by weight of the polyethylene is linear.

"Particles" means finely divided parts, and encompasses solid particles, liquid particles and plastic or waxy particles. Preferably, the particles are solid at a temperature of 25° C. or less. Preferably, the particles are liquid at a temperature of 80° C. or more in order to facilitate the preparation of the composition. The hydrophobic particles suitably have a mean diameter $D_{4,3}$ as measured by laser light scattering (using apparatus such as a MALVERN MASTERSIZER™) from 0.1 to 50 micrometers, preferably from 0.5 to 20 micrometers, more preferably from 1 to 10 micrometers.

Preferably, compositions of the invention include an emulsifier to facilitate the emulsification of the hydrophobic particles in the continuous aqueous phase and to stabilize the emulsion against coalescence of the hydrophobic particles. In general, the emulsifier is an anionic, cationic, non-ionic or zwitterionic surfactant. Preferably, the emulsifier is a non-ionic surfactant. Suitable non-ionic surfactants include alkyl ethers of polyethylene glycol and/or polypropylene glycol, including mixed ethers and mixtures thereof. The emulsifier is suitably present in an amount of from 2% to 10%, most preferably from 3% to 8% by weight of the composition.

The compositions of the invention, in addition to the hydrophobic particles and the aqueous continuous liquid phase, may also include other ingredients that are conventionally present in depilatory formulations, such as perfumes, oils, and pigments (such as titanium dioxide) and thickeners such as a clay.

Suitable clays for thickening may include organophilic and layered clay minerals belonging to the geological classes of the smectites, the kaolins, the illites, the chlorites, the attapulgites and the mixed layer clays. Typical examples of specific clays belonging to these classes are: 1) smectites, e.g., montmorillonite, bentonite, pyrophyllite, hectorite, saponite, sauconite, nontronite, talc, beidellite; 2) illites, e.g., bravaisite, muscovite, paragonite, phlogopite; 3) chlorites, e.g., corrensite, penninite, donbassite, sudoite; and 4) attapulgites, e.g., sepiolite, and polygorskyte.

The layered clay minerals may be either naturally occurring or synthetic. Preferred clay minerals for use in the present invention are natural or synthetic smectites and attapulgites (particularly the hectorites, montmorillonites and bentonites) and of these, the hectorites are especially preferred. Many of the above clays are available commercially, and typical examples of commercial hectorites are the LAPONITES™ from Laporte Industries Ltd., England; VEEGUM PRO™ and VEEGUM F™ from R. T. Vanderbilt, USA; and the Barasyms, MACALOIDS™ and Propaloids from Baroid Division, National Lead Company, USA. If a clay is used for thickening, it is preferably in an amount of from 0.1 to 10% by weight, more preferably from 0.1 to 1% by weight of the composition.

The inclusion of a clay, preferably sodium lithium magnesium silicate, is particularly advantageous, since this provides lithium, sodium and magnesium ions for the buffer system and improves the efficiency of depilation. It is particularly preferred if the clay is a synthetic hectorite clay such as LAPONITE™.

Other optional water-soluble thickening agents that may be used include CARBOMER™ (acrylic acid polymer, preferably cross-linked), acrylic polymer emulsions (e.g., acrylate/steareth-20 methracylate copolymer), polysaccharides, cellulose-based thickeners or natural thickeners such as gum arabic, alginates, carrageenan, locust bean gum, xanthan gum and polyvinyl alcohol. Mixtures of thickeners may be used.

A suitable method for preparing compositions according to the invention comprises the following steps:

1) Blending the fatty alcohol, emulsifier and oil-gelling agent together into a molten phase at a temperature of 75° C., preferably 85° C. or more, 2) emulsifying the molten phase into an aqueous phase, the temperature of the aqueous phase prior to emulsification being 60° C., preferably 70° C., more preferably 80° C. or more, whereby an emulsion comprising dispersed hydrophobic particles is formed, 3) cooling the emulsion to a temperature of 40° C. or less, 4) dispersing the depilatory agent and any accelerator in the emulsion.

The depilatory agent and any optional accelerator is preferably not added until after the emulsion has been cooled to prevent degradation of the depilatory agent (which may occur at substantially elevated temperatures). Any optional ingredients may be added thereafter; however, it is preferred for any clay to be added at an elevated temperature.

In an alternative process according to the invention, the temperature of the aqueous phase may be below 40° C., preferably below 25° C. prior to emulsification, whereby the temperature of the resulting emulsion, comprising dispersed particles, has a temperature of 40° C. or less, whereby no further cooling step is required prior to dispersing the depilatory agent and any accelerator in the emulsion. Alternatively, the depilatory agent and any optional accelerator may be present in the aqueous phase prior to the addition of the molten phase to the aqueous phase.

The second aspect of the invention provides a method of hair removal from human skin including the steps of i) applying a composition according to the first aspect of the invention to the skin where superfluous hair is present, ii) allowing the composition to remain in contact with the skin for a predetermined time, iii) removing the composition and degraded hair using a removal tool and iv) preferably washing the skin.

For this second aspect of the invention, it is preferred if the composition is applied to the skin with an application tool, giving the advantage that the composition does not come into contact with the user's hands. A block of material, such as a sponge or a spatula, may be employed, but a preferred application tool is a glove, mitt or thumbless mitt, preferably furnished with an inner layer or membrane that is impermeable to the composition. Preferably, the membrane is also impermeable to water.

The composition and degraded hair are preferably removed from the skin using a removal tool. A block of material, such as a sponge or a spatula, may be employed, but a preferred removal tool is a glove, mitt or thumbless mitt, preferably furnished with an inner layer or membrane that is impermeable to the composition. Preferably, the membrane is also impermeable to water.

It is particularly advantageous if the application tool and removal tool are provided as a combined tool that has two distinct sides, i.e., front and back, that are distinguishable by the user, one side being adapted to apply the composition to the skin, and the other side being adapted to remove the composition from the skin. This has the advantage that only a single combined tool is needed for the application and removal while minimizing or preventing contact of the user's hands with the composition and preventing accidental transfer of the composition to other parts of the body while ablutions are being performed. Preferably, the front and back faces of the tool are of distinctly different texture and/or color.

Preferably, the tool is a mitt or glove, more preferably a thumbless mitt, comprising an inner layer of a first material and an outer layer of a second material with an impermeable layer of flexible polymer membrane sandwiched between the inner and outer layers. Preferably, the front and back faces of the tool are of distinctly different texture and/or color. A thumbless mitt has the advantage that the user can apply the composition with the mitt on one hand, using the application side, then use the same mitt on the same hand for removal, using the removal side.

In an alternative embodiment, the tool may be in the form of a block of material, such as a rectangular parallelepiped or an ellipsoidal shape suitable to be held in the hand.

Preferably, the block is formed of two portions that are joined together, wherein one portion is adapted for application of the composition of the invention, and preferably is non-porous, and the other portion is adapted for removal of the composition and degraded hair, and is preferably porous and more preferably spongy, and is even more preferably furnished with a textured surface suitable for massaging or exfoliating the skin. Preferably, the portion adapted for application of the composition is substantially impermeable to water and to the composition.

According to the invention, there is further provided the use of a composition according to the invention to degrade hair keratin.

DETAILED DESCRIPTION OF THE INVENTION

Throughout this specification, percentages of ingredients by weight are referenced to the weight of the total composition, unless otherwise specified. The following Examples illustrate the invention.

Compositions were prepared according to the formulations given in the formulations table by emulsifying a melt at 85° C. formed from the cetearyl alcohol, ceteareth 20, ppg-15 stearyl ether and polyethylene (when present) into water at 80° C. The resulting blend was cooled to 40° C. prior to addition of the depilatory agent; other ingredients were blended while cooling from 80 to 40° C.

Examples 3A and 3B are compositions according to the invention. Examples 1, 2A and 2B are comparative examples. Examples 1, 2A, 2B, 3A and 3B were formulated such that the weight of fatty alcohol/emulsifier/polyethylene is substantially constant for each example.

| Formulation Table | | | | | | | | |
|---|---|---|---|---|---|---|---|---|
| Ingredient | Ex. 1 | Ex. 1B | Ex. 2A | Ex. 2B | Ex. 3A | Ex. 3B | Ex. 3C | Ex. 4 |
| Cetearyl alcohol | 5.5 | 5.5 | 9 | 9 | 7.8 | 7.8 | 7.8 | 7.8 |
| Ceteareth 20 | 2.2 | 2.2 | 3.6 | 3.6 | 3.1 | 3.1 | 3.1 | 3.1 |
| PPG-15 stearyl ether | 1.5 | 1.5 | 2.4 | 2.4 | 2.1 | 2.1 | 2.1 | 2.1 |
| PERFORMALENE 400 ™ polyethylene | — | — | — | — | 2 | 2 | 2 | — |
| PERFORMA V825 ™ Polyethylene | — | — | — | — | — | — | — | 2 |
| Urea | 8 | 8 | 8 | 8 | 8 | 8 | 8 | 8 |
| Thioglycolic acid | 3.1 | 3.1 | 4 | 4 | 4 | 4 | 4 | 4 |
| KOH | 3.8 | 3.8 | 5.9 | 5.9 | 5.9 | 5.9 | 5.9 | 5.9 |
| LAPONITE ™ | 0.5 | 0.5 | 0.2 | 0.2 | 0.2 | 0.2 | 0.2 | 0.2 |
| CaOH | 2.9 | 2.9 | 3.8 | 3.8 | 3.8 | 3.8 | 3.8 | 3.8 |
| Preservatives, Fragrance, Water | To 100 | To 100 | To 100 | To 100 | To 100 | To 100 | To 100 | To 100 |
| PH | 12-12.5 | 12-12.5 | 12-12.5 | 12-12.5 | 12-12.5 | 12-12.5 | 12-12.5 | 12-12.5 |

N.B. Formulas 1A and 1B have the same compositions but were made in different batches. Formulas 2A and 2B have the same compositions but made in different batches. Formulas 3A, 3B and 3C have the same compositions but were made in different batches.

PERFORMALENE 400™ has a mean molecular weight of 450 unified mass units, and PERFORMA V825™ has a mean molecular weight of 655.

The compositions according to Table 1 were stored at 25° C. in airtight containers for 24 hours prior to rinse-ability testing according to the following method.

Materials and Methods

The rinse-ability testing was carried out by applying a uniform layer of the cream being tested onto a glass plate, and subsequently measuring the volume of cream remaining on the glass plate after it had been exposed to a continuous flow of water for a pre-determined time.

The amount of cream remaining on the glass plate at the end of each trial is given as a percentage of cream remaining on the glass plate after the rinse-ability test is completed.

Test 1

Composition 3A was compared to composition 1. The results are given in Table 2.

TABLE 1

| Trial | % 3A remaining after 3 minutes rinsing | % 1A remaining after 3 minutes rinsing |
|---|---|---|
| 1 | 101.74 | 13.12 |
| 2 | 104.63 | 74.44 |
| 3 | 103.48 | 1.13 |
| 4 | 105.28 | 0.00 |
| 5 | 105.35 | 0.00 |
| 6 | 103.09 | 0.00 |
| Mean | 103.93 | 14.78 |
| Standard deviation | 1.415048632 | 29.67890707 |
| Standard deviation in % | 1.361564893 | 200.7704785 |

Test 2

Composition 3A was compared to composition 2A. The results are given in Table 2.

TABLE 2

| Trial | % 3A remaining after 3 minutes rinsing | % 1A remaining after 3 minutes rinsing |
|---|---|---|
| 1 | 101.12 | 1.03 |
| 2 | 99.72 | 2.25 |
| 3 | 102.62 | 69.92 |
| 4 | 100.68 | 10.32 |
| 5 | 101.82 | 0.54 |
| 6 | 83.97 | 24.26 |
| 7 | 101.74 | 3.38 |
| 8 | 95.97 | 0.00 |
| 9 | 102.35 | 36.65 |
| 10 | 99.35 | 10.57 |
| 11 | 101.22 | 30.46 |
| 12 | 99.29 | 48.23 |
| 13 | 103.14 | 35.15 |
| 14 | 102.20 | 64.28 |
| 15 | 67.22 | 30.99 |
| 16 | 101.43 | 49.68 |
| 17 | 101.44 | 42.45 |
| 18 | 98.17 | 71.79 |
| 19 | 101.04 | 8.53 |
| 20 | 101.25 | 47.28 |
| 21 | 102.35 | 33.76 |
| 22 | 101.62 | 67.59 |
| 23 | 101.07 | 69.06 |
| 24 | 100.26 | 0.00 |
| Mean | 98.79 | 31.59 |
| Standard deviation | 7.71831227 | 25.448937 |
| Standard deviation in % | 7.812600347 | 80.55881628 |

Test 3

Composition 3B was compared to composition 2B. The results are given in Table 3.

TABLE 3

| Trial | % 3B Remaining after 3 Minutes Rinsing | % 2B remaining after 3 Minutes Rinsing |
|---|---|---|
| 1 | 101.73 | 0.00 |
| 2 | 57.90 | 0.00 |
| 3 | 102.26 | 0.00 |
| 4 | 102.41 | 79.72 |
| 5 | 63.07 | 93.94 |
| 6 | 99.46 | 72.42 |
| 7 | 87.80 | 41.01 |
| Standard Deviation | 21.25121654 | 45.45926277 |
| Standard Deviation in % | 24.2029951 | 110.8368936 |

NB: up to 100% due to water remaining on the glass

Test 4

Composition 3B was compared to composition 4. The results are given in Table 4.

TABLE 4

| Trial | % 3B Remaining after 3 Minutes Rinsing | % 4 remaining after 3 Minutes Rinsing |
|---|---|---|
| 1 | 47.46 | 28.13 |
| 2 | 21.84 | 6.63 |
| 3 | 104.01 | 0.00 |
| 4 | 101.77 | 4.86 |
| 7 | 103.17 | 0.00 |
| 8 | 104.19 | 22.89 |
| Mean | 80.41 | 10.42 |
| Standard Deviation | 36.37008368 | 12.09636998 |
| Standard Deviation in % | 45.23236471 | 116.1010269 |

Test 5

Composition 3C was compared to composition 1B. The results are given in Table 5.

TABLE 5

| Trial | % 3C Remaining after 3 Minutes Rinsing | % 1B remaining after 3 Minutes Rinsing |
|---|---|---|
| 3 | 102.92 | 0 |
| 4 | 101.63 | 0 |
| 5 | 103.76 | 13.18 |
| 7 | 101.4 | 76.19 |
| 8 | 62.23 | 8.49 |
| 9 | 103.36 | 0 |
| Mean | 95.88 | 16.31 |
| Standard Deviation | 16.51275112 | 29.84864771 |
| Standard Deviation in % | 0 | 183.0080998 |

The results demonstrate that:

1) The presence of the polyethylene leads to a marked increase in rinsing time for the compositions.

2) The polyethylene of molecular weight 400 is more effective than that of molecular weight 655, however polyethylene at both molecular weights show reduced rinse-ability.

The invention claimed is:

1. A depilatory composition comprising an emulsion of solid hydrophobic particles in a continuous aqueous phase,
    wherein the continuous aqueous phase comprises a depilatory agent;
    wherein the solid hydrophobic particles comprise a mixture of a fatty alcohol and an oil-gelling agent; and
    wherein the oil-gelling agent is a polyethylene homopolymer which has a molecular weight from 300 to 600 unified mass units.

2. The depilatory composition according to claim 1, comprising from 3 to 20% by weight of the fatty alcohol and 0.2 to 5% by weight of the oil-gelling agent.

3. The depilatory composition according to claim 1, wherein the fatty alcohol has an alkyl chain comprising from 8 to 22 carbon atoms.

4. The depilatory composition according to claim 1, wherein, the depilatory agent is a sulfhydryl compound.

5. The depilatory composition according to claim 1, comprising from 1 to 8% by weight of the depilatory agent, expressed as the equivalent acid form of the depilatory agent.

6. A method for preparing the depilatory composition according to claim 1, comprising:
    blending the fatty alcohol, emulsifier and oil-gelling agent together into a molten phase at a temperature of 75° C. or more;
    emulsifying the molten phase into an aqueous phase, the temperature of the aqueous phase prior to emulsification being 60° C. or more, whereby the emulsion comprising the dispersed solid hydrophobic particles is formed;
    cooling the emulsion to a temperature of 40° C. or less; and
    dispersing the depilatory agent in the emulsion.

7. The depilatory composition according to claim 1, the solid hydrophobic particles having a mean diameter from 0.1 to 50 micrometers.

8. A depilatory composition comprising an emulsion of homogeneous hydrophobic particles in a continuous aqueous phase,
    wherein the continuous aqueous phase comprises a depilatory agent,
    wherein the homogeneous hydrophobic particles comprise a mixture of a fatty alcohol and an oil-gelling agent; and
    wherein the oil-gelling agent is a polyethylene homopolymer which has a molecular weight from 300 to 600 unified mass units.

9. The depilatory composition according to claim 8, comprising from 3 to 20% by weight of the fatty alcohol and 0.2 to 5% by weight of the oil-gelling agent.

10. The depilatory composition according to claim 8, wherein the fatty alcohol has an alkyl chain comprising from 8 to 22 carbon atoms.

11. The depilatory composition according to claim 8, wherein, the depilatory agent is a sulfhydryl compound.

12. The depilatory composition according to claim 8, comprising from 1 to 8% by weight of the depilatory agent, expressed as the equivalent acid form of the depilatory agent.

13. The depilatory composition according to claim 8, the homogeneous hydrophobic particles having a mean diameter from 0.1 to 50 micrometers.

14. A method for preparing the depilatory composition according to claim 8, comprising:
    blending the fatty alcohol, emulsifier and oil-gelling agent together into a molten phase at a temperature of 75° C. or more;
    emulsifying the molten phase into an aqueous phase, the temperature of the aqueous phase prior to emulsification being 60° C. or more, whereby the emulsion comprising the dispersed homogeneous hydrophobic particles is formed;
    cooling the emulsion to a temperature of 40° C. or less; and
    dispersing the depilatory agent in the emulsion.

* * * * *

UNITED STATES PATENT AND TRADEMARK OFFICE
CERTIFICATE OF CORRECTION

| | |
|---|---|
| PATENT NO. | : 8,545,825 B2 |
| APPLICATION NO. | : 11/660817 |
| DATED | : October 1, 2013 |
| INVENTOR(S) | : Farid Moussouni |

It is certified that error appears in the above-identified patent and that said Letters Patent is hereby corrected as shown below:

On the Title Page, item (73) should read: Assignee: Reckitt Benckiser (UK) Limited Signed and Sealed this
Fourth Day of March, 2014

Michelle K. Lee
*Deputy Director of the United States Patent and Trademark Office*